United States Patent [19]

Nacken et al.

[11] Patent Number: 5,952,195

[45] Date of Patent: Sep. 14, 1999

[54] PROMOTERS FOR EXPRESSING PROTEINS OF INTEREST IN YEAST

[75] Inventors: Valérie Nacken, Strasbourg, France; Tilman Achstetter, Oberkirch, Germany

[73] Assignee: Transgene S.A., Strasbourg, France

[21] Appl. No.: 08/930,617

[22] PCT Filed: Apr. 5, 1996

[86] PCT No.: PCT/FR96/00523

§ 371 Date: Mar. 9, 1998

§ 102(e) Date: Mar. 9, 1998

[87] PCT Pub. No.: WO96/31611

PCT Pub. Date: Oct. 10, 1996

[30] Foreign Application Priority Data

Apr. 7, 1995 [FR] France ................................. 95 04171

[51] Int. Cl.[6] ............................ C12P 21/02; C07H 21/04; C12N 15/63

[52] U.S. Cl. .................. 435/69.1; 435/69.2; 435/69.3; 435/69.4; 435/69.5; 435/69.6; 435/69.9; 435/320.1; 435/440; 536/23.1; 536/24.1

[58] Field of Search .................................. 536/24.1, 23.1; 435/69.1, 320.1, 69.9, 69.2, 69.3, 69.4, 69.5, 69.51, 69.52, 69.6, 172.1, 172.3, 254.11, 254.2, 254.21, 254.23, 255.2, 255.21, 255.5, 255.6, 440

Primary Examiner—Nancy Degen
Attorney, Agent, or Firm—Burns, Doane, Swecker & Mathis, L.L.P.

[57] ABSTRACT

The present invention provides novel nucleic acid fragments isolated from the genomic DNA of yeast and having transcription promoter activity, as well as expression cassettes, vectors, and host cells containing said nucleic acid fragments. The present invention also provides methods for incorporating the nucleic acid fragments of the present invention for producing commercially or therapeutically useful polypeptides.

18 Claims, 7 Drawing Sheets

PROMOTERS FOR EXPRESSING PROTEINS OF INTEREST IN YEAST

The present invention relates to the field of biotechnology, in particular to an improvement made to the production of a polypeptide of commercial or therapeutic interest in yeast and, in particular, in *Saccharomyces cerevisiae*. It also relates, firstly, to new nucleic acid fragments isolated from the genomic DNA of *Saccharomyces cerevisiae* and having a transcriptional promoter activity and, secondly, expression cassettes, expression vectors and host cells containing them as well as their use for the production of polypeptides of interest.

The yeast *Saccharomyces cerevisiae* is considered as one of the preferred hosts for the production of recombinant proteins for numerous reasons. On the one hand, this organism is nonpathogenic and it is commonly used in the food industry. On the other hand, it can be cultured on a large scale and at high density in a relatively inexpensive medium and can be easily adapted to an industrial environment. Furthermore, it has been particularly studied, such that many data relating to its genetics and its physiology are available. Finally, it is capable of carrying out certain typically eukaryotic modifications (glycosilation, disulfide bridges and the like).

Although numerous transcriptional promoters which are functional in yeasts have been described in the literature, only some of them have proved effective for the production of polypeptides by the recombinant route. There may be mentioned in particular the promoters of the PGK genes (3-phosphoglycerate kinase; Hitzeman et al., 1983, Science, 219, 620–625), TDH genes encoding GAPDH (Glyceraldehyde phosphate dehydrogenase; Holland and Holland, 1979, J. Biol. Chem., 254, 9839–9845), TEF1 genes (Elongation factor 1; Cottrelle et al., 1985, J. Biol. Chem., 260, 3090–3096), MFα1 (α sex pheromone precursor; Inokuchi et al., 1987, Mol. Cell. Biol., 7, 3185–3193) which are considered as strong constitutive promoters or alternatively the regulatable promoter CYC1 which is repressed in the presence of glucose (Guarente and Ptashne, 1981, Proc. Natl. Acad. Sci. USA, 78, 2199–2203) or PHO5 which can be regulated by thiamine (Meyhack et al., 1982, EMBO J., 1, 675–680). However, for reasons which are often unexplained, they do not always allow the effective expression of the genes which they control and therefore the production of polypeptides at high levels. In this context, it is always advantageous to be able to have new promoters in order to generate new effective host/vector systems for the production of a large quantity of proteins of interest. Furthermore, having a choice of effective promoters in a given cell also makes it possible to envisage the production of multiple proteins in this same cell (for example several enzymes of the same metabolic chain) while avoiding the problems of recombination between homologous sequences.

In general, a promoter region is situated in the 5' region of the genes and comprises all the elements allowing the transcription of a DNA fragment placed under their control, in particular:

(1) a so-called minimal promoter region comprising the TATA box and the site of initiation of transcription, which determines the position of the site of initiation as well as the basal level of transcription. In *Saccharomyces cerevisiae*, the length of the minimal promoter region is relatively variable. Indeed, the exact location of the TATA box varies from one gene to another and may be situated from −40 to −120 nucleotides upstream of the site of the initiation (Chen and Struhl, 1985, EMBO J., 4, 3273–3280)

(2) sequences situated upstream of the TATA box (immediately upstream up to several hundreds of nucleotides) which make it possible to ensure an effective level of transcription either constitutively (relatively constant level of transcription all along the cell cycle, regardless of the conditions of culture) or in a regulatable manner (activation of transcription in the presence of an activator and/or repression in the presence of a repressor). These sequences, subsequently designated modulatory sequences, may be of several types: activator, inhibitory, enhancer, inducible, repressible and may respond to cellular factors or varied culture conditions.

Three genomic sequences of *Saccharomyces cerevisiae* have now been isolated and characterized and their transcription promoter function demonstrated. Placed upstream of a reporter gene (gene for resistance to phleomycin or GUS gene encoding β-glucuronidase), each of these sequences allows its expression in the yeast *Saccharomyces cerevisiae* and, in the case of two of them, at a high level since greater than or roughly equivalent to that detected with reputedly strong promoter regions such as those of the PGK and MFα1 genes. Comparison with data banks indicate that two of the cloned sequences are new and do not feature in the data banks accessible to the public (SEQ ID NO: 1 and 2). As regards the third (SEQ ID NO: 3), it corresponds to a sequence located in 3' of the yeast gene COX 4 in a region where the presence of a promoter is unexpected. The present invention provides an advantageous solution to the problem of the production of proteins of interest by the recombinant route.

Consequently, the subject of the present invention is an isolated nucleic acid fragment comprising all or part of a nucleotide sequence homologous to the sequence shown in the sequence identifier NO: 1, 2 or 3 or homologous to its complementary, said fragment having a transcriptional promoter activity.

"Nucleic acid fragment" is understood to mean a nucleotide polymer which may be of the DNA or RNA type. These terms are defined in all basic molecular biology manuals. Preferably, a nucleic acid fragment according to the invention is a double-stranded DNA fragment.

In general, all or part of one of the nucleotide sequences specified in SEQ ID NO: 1, 2 and 3, its complementary or one of its homologues may be used within the framework of the present invention. The term "part" designates a fragment comprising a portion of at least 17 continuous nucleotides identical to a portion of length equivalent to one of the nucleotide sequences indicated in the sequence identifiers or to its complementary. However, of course, a nucleic acid fragment according to the invention is not limited to the sequences described and may extend beyond.

The term "homologous" means a sequence capable of hybridizing, under stringent conditions, with all or part of the sequence reported in SEQ ID NO: 1, 2 or 3. It refers more particularly to any nucleic acid retaining the promoter function and exhibiting one or more sequence modifications in relation to one of these sequences. These modifications may be obtained by mutation, deletion and/or addition of one or more nucleotides in relation to the native sequence. They can be introduced in particular in order to improve the promoter activity, to suppress a transcription inhibiting region, to make a constitutive promoter regulatable or vice versa, to introduce a restriction site facilitating subsequent cloning steps, to eliminate the sequences which are not essential to the transcriptional activity, and the like. In this context, a degree of homology of 70% relative to the native sequence, advantageously of 80% and, preferably, of 90%, will be preferred. Persons skilled in the art know where to carry out the modifications so as not to drastically alter the transcription promoter function and they will avoid in particular the site of initiation of transcription and the TATA box. They also know the techniques which make it possible to evaluate whether the homologue generated has a promoter activity, for example by inserting upstream a reporter gene whose expression is easily detectable (β-galactosidase, catechol oxygenase, luciferase or alternatively a gene conferring resistance to an antibiotic). However, any other conventional technique can also be used.

According to a preferred embodiment, a nucleic acid fragment according to the invention is identical to all or part of one of the nucleotide sequences shown in the sequence identifier NO: 1, 2 or 3 or of its complementary.

By way of preferred but nonlimiting examples, it may be envisaged using a nucleic acid fragment having a sequence as shown in:

(i) the sequence identifier NO: 1, starting at the nucleotide in position 462 and ending at the nucleotide in position 1016, or (ii) the sequence identifier NO: 1, starting at the nucleotide in position 197 and ending at the nucleotide in position 1016, or (iii) the sequence identifier NO: 3, starting at the nucleotide in position 5 and ending at the nucleotide in position 523.

For the purposes of the present invention, a nucleic acid fragment according to the invention may consist of the assembly of elements of various origins to form a so-called hybrid promoter which is functional in the host cell considered. In particular, such a hybrid promoter may comprise:

(i) a nucleic acid fragment according to the invention, comprising a minimal promoter region; said minimal promoter region being placed downstream of one or more modulatory sequences heterologous to said minimal promoter region, or (ii) a nucleic acid fragment according to the invention, comprising at least one modulatory sequence; said modulatory sequence being placed upstream of a minimal promoter region heterologous to said modulatory sequence.

According to an embodiment of the first variant, use may be made of one or more regulatable modulatory sequences in order to generate a regulatable hybrid promoter from which transcription may be induced or repressed according to the conditions used. This specific embodiment is particularly advantageous in the context of the production of proteins of interest exhibiting a degree of toxicity towards the host cell. There will be preferably chosen regulatable modulatory sequences which make it possible to vary the transcription according to the culture conditions or the growth phase. In general, such sequences are obtained or derived from regulatable genes and are known to persons skilled in the art. As a guide, there may be mentioned those derived from the CYC1 gene which can be regulated by glucose, from the PHO5 gene which can be regulated by thiamin, or from the GAL1, GAL7 and GAL10 genes which can be regulated by galactose. It goes without saying that these sequences may comprise modifications (mutation, deletion and/or substitution of one or more nucleotides) relative to the native sequence, as long as they do not drastically alter their modulatory function.

It is also indicated that a nucleic acid fragment according to the invention may be used as a bi-directional promoter capable of exerting its function independently of its orientation in relation to the gene to be transcribed (in a sense orientation from 5' to 3' as indicated in the SEQ IDs or conversely).

Of course, a nucleic acid fragment according to the invention can be obtained by any technique in use in the art, for example by cloning, hybridization with the aid of an appropriate probe, by PCR (Polymerase Chain Reaction) with the aid of suitable primers or alternatively by chemical synthesis.

In accordance with the aims pursued by the present invention, a nucleic acid fragment according to the invention is intended to allow the expression of a gene of interest in a host cell and, to this effect, is operably linked thereto in an expression cassette. Accordingly, the present invention also extends to an expression cassette comprising a nucleic acid fragment according to the invention and a gene of interest placed under its control. It goes without saying that an expression cassette according to the invention may contain several genes of interest either within the framework of a multicistronic cassette (schematically represented by the "promoter-gene 1-gene 2 . . . "arrangement) in which the different genes are placed downstream of a nucleic acid fragment according to the invention and are separated from each other by appropriate sequences, such as the IRES (for Internal Ribosome Entry Site) elements allowing the reinitiation of translation or alternatively within the framework of a bidirectional cassette ("gene 1-promoter-gene 2") in which a nucleic acid fragment according to the invention is inserted between two genes of interest in order to control their expression simultaneously.

For the purpose of the present invention, a gene of interest may be derived from a eukaryotic or prokaryotic organism or from a virus. It can be isolated by any conventional molecular biology technique or can be synthesized by the chemical route. Moreover, it can encode a protein of interest which is (i) intracellular, (ii) membrane-bound or anchored to the cell membrane or (iii) secreted in the culture medium. It may therefore comprise additional elements such as, for example, a sequence encoding a secretion signal. By way of examples, there may be indicated the signal sequence BGL2 (EP 0 423 302), the pre- or pre-pro sequences MFα1 (Kurjan and Herskowitz, 1982, Cell, 30, 933–943) and also the defensin A pro sequence (EP 0 607 080). Use can also be made of the endogenous secretory signals of the gene considered. The choice of the secretory signals which may be envisaged within the framework of the present invention is within the capability of persons skilled in the art.

Moreover, a gene of interest may encode a polypeptide of interest corresponding to all or part of a protein as found in nature (native or truncated protein). It may also be a chimeric protein, for example coming from the fusion of polypeptides of diverse origins or from a mutant exhibiting improved and/or modified biological properties. Such a mutant can be obtained by conventional molecular biology techniques. Among the proteins or polypeptides of interest, there may be mentioned by way of nonlimiting examples:

cytokines and in particular interleukins (IL-2, 4, 5, 6, 12 and the like), α-, β- and γ-interferons, colony stimulating factors (GM-CSF, C-CSF, M-CSF);

growth factors (growth hormone, erythropoietin, insulin and the like) or cellular or nuclear receptors;

anticoagulants, preferably hirudin and, in particular, the hirudin variants described in European Application EP 273 800 and, most preferably, the variant HV2 Lys47;

enzymes (trypsin, ribonucleases, P450 cytochromes, lipases, amylases and the like);

structural proteins (albumin and the like);

enzyme inhibitors (α-1-antitrypsin, antithrombin III, viral protease inhibitors and the like);

polypeptides capable of inhibiting the initiation or progression of tumors or cancers (inhibitors acting at the level of cell division or of transduction signals, products of expression of tumor suppresser genes, for example p53 or Rb and the like); and polypeptides capable of inhibiting a viral, bacterial or parasitic infection and/or its development (antigenic polypeptides having immunogenic properties, antibodies, trans-dominant variants capable of inhibiting the action of the native protein by competition and the like).

Of course, an expression cassette according to the invention may, in addition, comprise additional elements necessary for the expression of the gene of interest (intron sequence, transcription terminator sequence and the like) or alternatively for its maintenance in the host cell considered (replication origin such as ARS or 2μ, gene encoding a phenotype selectable marker such as URA3 or LEU2, gene encoding a product conferring resistance to an antibiotic, for example hygromycin, cycloheximide, neomycin, phleomycin and the like). Such elements are known to persons skilled in the art.

The invention also relates to an expression vector comprising one or more expression cassettes according to the invention. It may be a multicopy or centromeric plasmid vector, a cosmid or a YAC-type vector. Finally, it may be integrative or self-replicating.

The present invention also relates to a host cell comprising an expression cassette or a vector according to the invention. It may be generated by any method which makes it possible to introduce a foreign DNA into a cell (transformation, transfection, microinjection, electroporation, liposomes and the like). It is indicated that any host cell, eukaryotic or prokaryotic, may be used within the framework of the present invention as long as it has the factors appropriate to allow a nucleic acid fragment according to the invention to exert its promoter function. It is within the capability of persons skilled in the art to check if a particular cell can be used as host by measuring the promoter activity as indicated above.

A host cell according to the invention may be derived from an animal cell (CHO, Vero, BHK and the like) or from a bacterium such as *Escherichia coli*, but use will be preferably made of a lower eukaryot and, in particular, a yeast. To this end, there may be used a yeast of the genus Saccharomyces, Schizosaccharomyces, Pichia, Kluyveromyces, Hansenula, Phaffia or Yarrowia. Advantageously, it may be chosen from the species *Schizosaccharomyces pombe, Pichia pastoris, Kluyveromyces lactis, Hansenula polymorpha, Yarrowia lipolytica* and, preferably, *Saccharomyces cerevisiae*. The use of a yeast deficient in protease(s) such as TGY73.4 or that described in European Application EP 390 676 is most particularly preferred. A large number of these strains are commercially available in establishments such as AFRC (Agriculture and Food Research Council, Norfolk, UK) and ATCC (Rockville, Mass., USA).

Finally, the subject of the present invention is also a process for the production of a polypeptide of interest comprising the culture of a host cell according to the invention under appropriate culture conditions allowing the production of said polypeptide of interest and its recovery from the cellular culture. A defined culture medium comprising glucose as carbon source is preferably used.

Within the framework of the present invention, this process is preferably applicable to the production of a protein of therapeutic interest and, in particular, hirudin, in a yeast *Saccharomyces cerevisiae*. The protein may be recovered directly from the culture medium or after lysis of the cells according to conventional methods. It can be purified by applying standard techniques known to persons skilled in the art, for example ion-exchange chromatography, differential precipitation, immunopurification or alternatively gel filtration at high or low pressure.

EXAMPLES

The examples below will make it possible to demonstrate other characteristics and advantages of the present invention. These examples are illustrated with reference to the following figures:

Figure 1:
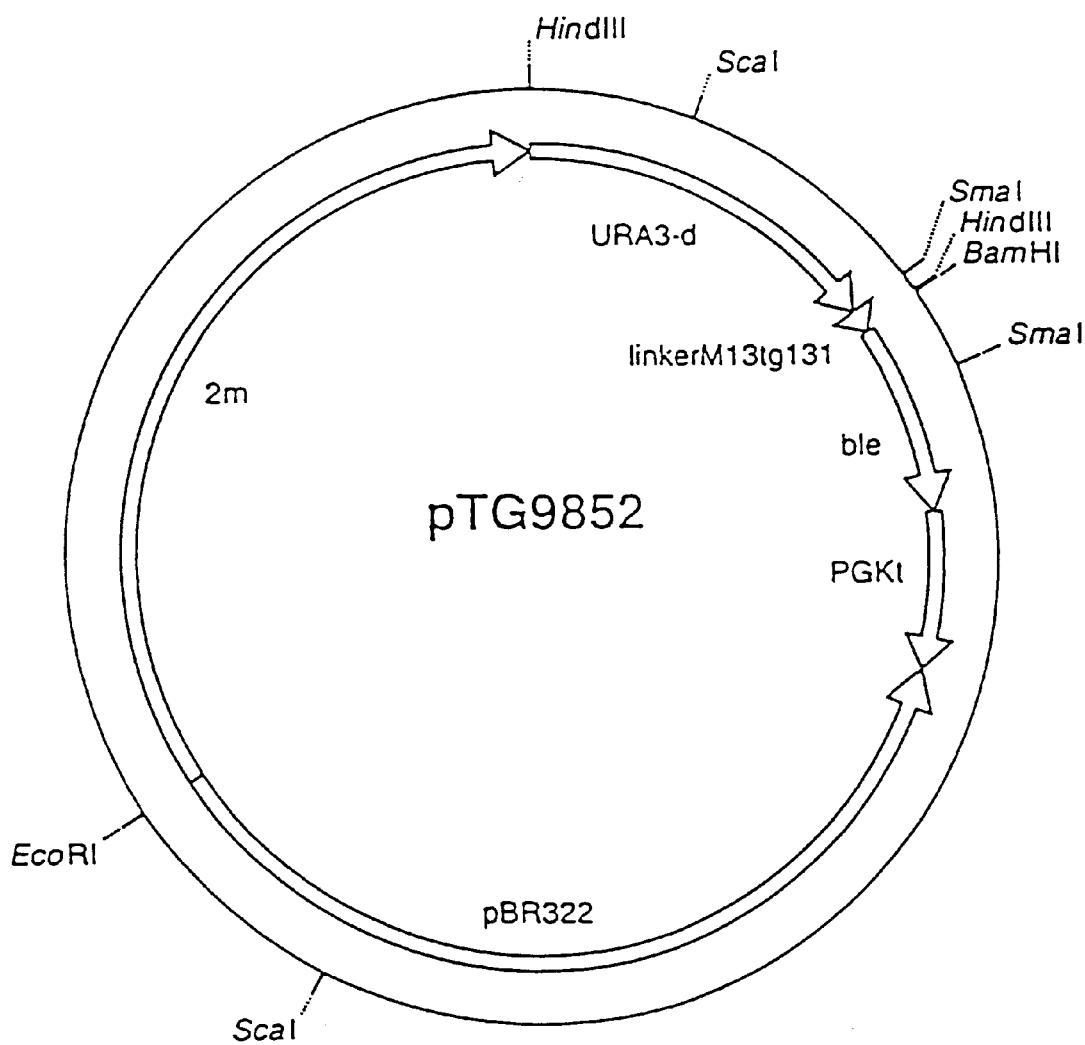
FIG. 1 is a schematic representation of the vector pTG9852 for the selection of DNA fragments having a transcriptional promoter activity. It comprises the URA3-d gene, a multiple cloning site (derived from M13tg131; Kieny et al., 1983, Gene, 26, 91–99), the ble gene conferring resistance to phleomycin, the transcription terminator of the PGK gene (PGKt), a fragment of pBR322 carrying a bacterial replication origin and the Amp gene conferring resistance to ampicillin and the replication origin 2μ (indicated 2m).

The techniques described below are carried out according to the general genetic engineering and molecular cloning techniques detailed in Maniatis et al. (1989, Laboratory Manual, Cold Spring Harbor Laboratory Press, Cold Spring Harbor, N.Y.) or according to the recommendations of the manufacturer when a commercial kit is used. The cloning steps in the bacterium are performed in the *Escherichia coli*

(*E. coli*) 5K strain (Hubacek and Glover, 1970, J. Mol. Biol., 50, 111–127). The PCR amplification techniques are known to persons skilled in the art (see for example PCR Protocols, A Guide to Methods and Applications, 1990, ed Innis, Gelfand, Sninsky and White, Academic Press Inc). As regards the repair of the restriction sites, the technique used consists of filling the protruding 5' ends with the aid of the large *E. coli* DNA polymerase I fragment (Klenow).

As regards the technology applied to the yeasts, it is abundantly described in Rose et al. (1990, Methods in Yeast Genetics: A Laboratory Course Manual, Cold Spring Harbor Laboratory Press, Cold Spring Harbor, N.Y.). The *Saccharomyces cerevisiae* strains are transformed by electroporation. However, any other standard technique can be used. As regards the culture conditions, the yeasts not transformed are generally cultured at 28° C. in nonselective YPG medium (yeast extract 1%, bactopeptone 1% and glucose 2%) whereas the cells transformed are maintained under selective conditions depending on the nature of the selectable gene contained in the construct. For example, when the selectable marker consists of the ble gene conferring resistance to phleomycin, the culture is carried out in YEG medium (yeast extract 0.5%, glucose 2%) buffered to pH7 by addition of 0.1 M MOPS and in the presence of phleomycin at a minimum concentration of 50 µg/ml. When the URA3 or URA3-d (complementation of a uracil auxotrophy) gene is used, the culture medium is composed of YNBG+cas (yeast nitrogen base 0.675%, glucose 1% and casamino acids 0.5%)

Example 1

Cloning of yeast DNA fragments having a promoter activity

A. Preparation of chromosomal DNA IX

A DNA library enriched with DNA fragments obtained from chromosome IX is constituted from the yeast *Saccharomyces cerevisiae* TGY73.4 (MATα, ura3, his3, pral, prbl, prcl, cpsl) treated by the so-called in solid agarose technique (Rose et al; 1990, supra, Preparation of chromosome-size yeast DNA molecules in solid agarose). Briefly, the yeasts treated with zymolyase are included in the agarose which is then solidified. Next, the chromosomes are separated by pulsed-field electrophoresis (CHEF-DRII, Biorad) on a 1% agarose gel (Biorad chromosomal grade agarose) in 0.5× TBE buffer (45 mM Tris-HCl, 45 mM Borate and 2 mM EDTA). The electrophoresis is carried out for a total duration of 24 hours (h), applying the following parameters: pulses of 40 sec for 16 h and then of 90 sec for 8 h with a voltage of 200 volts. These conditions are optimal for the separation of chromosomes of small size (I, VI, III and IX). The band corresponding to chromosome IX (the fourth from the bottom) is cut out of the gel and the DNA extracted from the agarose (GeneClean kit, Bio 101 Inc). It was necessary to carry out several electrophoreses of this type in order to be able to have about 1 µg of chromosomal DNA.

Southern analysis (Southern, 1974, J. Mol. Biol., 98, 503–517) by testing a labeled aliquot of this preparation (DIG DNA labeling and detection kit, Boehringer) on a replica of the gel of yeast chromosomes confirms the enrichment with chromosome IX.

B. Construction of a yeast IX chromosomal DNA library

The preparation enriched with chromosome IX is partially digested with the enzyme Sau3A (10 digestions of 100 ng of DNA with 0.2 unit of enzyme for 1 h at 37° C. in a reaction volume of 50 µl). The enzyme reaction is stopped by adding 1 µl of 0.5 M EDTA at pH8. After alcohol precipitation, the fragments of a size of between 0.5 and 1.5 kb are isolated on 1% LMP agarose gel (Low Melting Point, BRL) and eluted by the GeneClean method.

The isolated fragments are cloned into the plasmid pTG9852 (FIG. 1) linearized with BamHI and treated with calf alkaline phosphatase (Boehringer). The latter is derived from the plasmids pTG6888 and pUT332 (Gatignol et al., 1987, Mol. Gen. Genet., 207, 342–348). The first corresponds to the vector pTG3828 (Achstetter et al., 1992, Gene, 110, 25–31) modified by suppression of the XbaI site contained in the 2µ origin (by partial XbaI digestion and treatment with Klenow). In parallel, the coding part of the ble gene is purified from pUT332 in the form of a BamHI-EcoRI fragment which is subjected to the action of Klenow before being introduced into the BglII site (made blunt by treating with Klenow) of the vector pTG6888. The insertion of the DNA fragments into pTG9852 at the level of the unique BamHI site placed upstream of the coding sequences of the ble gene, will make it possible to select those which have a transcriptional promoter activity (by selecting yeasts transformed on phleomycin).

Fifteen series of transformations by electroporation of the *E. coli* 5K strain were carried out and made it possible to generate 10930 clones resistant to ampicillin, and therefore transformed. Given the size of the inserts selected (0.5 to 1.5 kb) and the size of chromosome IX (450 kb), the number of clones obtained is quite representative of the DNA library (factor of about 20 times). A sample of colonies is analyzed by PCR. The primers oTG5427 and oTG5428 (SEQ ID NO: 4 and 5) are used under the following conditions (30 cycles: denaturation 30 sec at 90° C., annealing 2 min at 54° C. and extension 2 min at 72° C.). In the absence of insert (parental vector pTG9852), the amplification generates a 269 bp band. In contrast, after insertion of a yeast fragment, the size of the amplified band is increased by the size of the insert. The results indicate a frequency of insertion of 90% and a mean size of the inserts of close to 700 bp.

A library is constituted by extracting the plasmid content of all the clones generated.

C. Selection of potential promoters which are functional in the yeast *Saccharomyces cerevisiae*

The library obtained in the preceding step is transformed in the yeast strain TGY74.3 by electroporation in dishes with an interface of 2 mm (Cellject system, Eurogentic; voltage 1000 V, resistance 412Ω and capacitance 40 µF in a single pulse mode).

The electroporated cells are spread in parallel on two different media in order to evaluate, on the one hand, if they are transformed (spreading on YNBG+cas medium for the selection of the Ura$^+$ phenotype) and, on the other hand, if the insert has a transcriptional promoter activity (spreading on YEG medium supplemented with 250 µg/ml of phleomycin). It is indicated that the strain TGY73.4 non-transformed or transformed by the vector pTG9852 (carrying the ble gene lacking a promoter) is incapable of growing above a phleomycin concentration of 20 µg/ml. By way of comparison, the vector pTG9851 comprising a cassette for functional expression of the ble gene (under the control of the TEF1 promoter) can withstand an antibiotic concentration of 2 mg/ml. This is obtained by introducing the BamHI fragment isolated from the vector pUT332 into the BglII site of pTG6888. On the other hand, when the promoter used is weak (pTG9895 comprising the ble gene under the control of the promoter of the KEX2 gene; see Example 2), the cells grow up to 50 µg/ml. Thus the selected concentration of 250 µg/ml is intermediate in order to be able to select promoter fragments of variable strength.

9300 transformants (Ura$^+$) are generated, of which about 1% exhibit resistance to a phleomycin concentration of 250

μg/ml (106 clones). PCR analysis with the preceding primers indicates a frequency of inserts of 80%, their size varying from 0.5 to 1.6 kb with a mean towards 0.7–0.8 kb.

Replicas of these 106 candidates were made on selective medium with increasing phleomycin concentration and 20 clones are resistant to 2 mg/ml. In order to check that their resistance is not due to a spontaneous mutation, the plasmid content of the 20 transformants selected is electroducted in *E. coli* 5K (Nacken et al., 1994, Nucleic, Acids Res., 22, 1509–1510) before being reintroduced into the yeast TGY73.4. Four clones still exhibit a band amplifiable by PCR and a capacity for growth in the presence of phleomycin. Three of them were characterized. They are clones transformed with the plasmids pTG8732, pTG8733 and pTG8734 carrying the inserts D64, R13 and J1 respectively.

Southern analysis of a replica of a gel of yeast chromosomes (Example 1A) with the aid of labeled inserts indicates that R13 is derived from chromosome IX.

D. Analysis of the inserts selected.

Their sequence was determined directly on double-stranded plasmids according to the technique of Sanger et al. (1977, Proc. Natl. Acad. Sci. USA, 74, 5463–5467). Analysis of the data shows the presence of transcriptional consensus elements (see Table 1).

(J1) and with the aid of primers provided with a ClaI restriction site in 5' of the sense primer and a SalI restriction site in 5' of the antisense. These are indicated in the sequence identifiers 6 to 9 (oTG6302 and oTG6293 for D64; oTG6292 and oTG6293 for R13 and oTG6298 and oTG6293 for J1).

B. Characterization of subfragments of the inserts selected.

Since the insert R13 exceeds 1 kb, it may be useful to have subfragments of a smaller size, and therefore easier to handle and retaining nonetheless a transcriptional promoter activity. The 5' and 3' regions of R13 are isolated from pTG8733 with the aid of the primers oTG6292 and oTG6294 (SEQ ID NO: 10) and oTG6301 (SEQ ID NO: 11) and oTG6293 respectively. The 416 bp fragment covering the 5' part is designated R13.2 whereas that corresponding to the 3' half, with a length of 599 bp, is called R13.3. Other subfragments were created by progressive deletion of the 5' region (see Example 5 below).

In the case of J1, the insert is deleted in 3' in order to eliminate the putative ORF of 25 aa and, in particular, its initiator ATG capable of interfering with the translation of the protein of interest. A 547 bp fragment (J1.2) lacking putative coding sequences is isolated by amplification from pTG8374 and the primers oTG6298 and oTG6299 (SEQ ID NO: 12).

TABLE 1

| Plasmid | Insert | SEQ ID | CAATC[1] | TATAW[1] (W = A or T) | YYYYYYYY[1] (Y = C or T) | CAAG | CASACA[1] (S = G or C) |
|---|---|---|---|---|---|---|---|
| pTG 8732 | D64 | 2 | 343, 395, 551c | 578, 579c | 282, 320, 331, 379, 186c, 221c, 265c, 608c | 96, 4c, 405c, 444c, 566c, 573c | — |
| pTG 8733 | R13 | 1 | 162, 279 | 654, 831, 179c, 185c, 192c, 552c, 653c | 113, 144, 451, 902, 91c, 128c, 336c, 351c | 205, 269, 613, 751, 771, 538c | 245 |
| pTG 8734 | J1 | 3 | — | 20, 19c, 462c | 186, 294, 6c, 214c, 325c, 342c, 556c | 299c, 426c | — |

Legend:
The positions are given relative to the first nucleotide (in the 5' - 3' direction) of the corresponding SEQ ID, or, when it is indicated, of the complementary strand.
[1]: For further details on the CAAT box and TATA box units rich in C and T, and for the CAAG and CASACA units, refer to Dobson et al. (1982, Nucleic Acids Res., 10, 2625–2637)

Comparison with the sequences of the Genbank data bank shows that the inserts D64 and R13 carry a sequence not listed so far. As regards J1, it corresponds to sequences situated in 3' of the *Saccharomyces cerevisiae* COX4 gene, in a region where the presence of a promoter is unexpected since it is situated downstream of coding sequences.

As regards the search for putative reading frames (ORF), the presence of an ORF of 96 amino acids (aa) in the first 5' half of D64 and of two small-sized ORFs (57 and 25 aa) covering respectively the 5' and 3' ends of J1, is noted.

Example 2

Vector for expressing the GUS gene under the control of the preceding inserts.

The activity of the transcriptional promoter is evaluated in relation to the GUS gene whose product of expression can be easily measured. Indeed, its enzymatic activity can be detected by colorimetry, fluorometric assay on cellular extracts (Jefferson et al., 1987, Molecular Biology Reporter, 5, 387–405) or by histochemical test on Nylon filters (Hirt, 1991, Current Genetics, 20, 437–439).

A. Isolation of the inserts selected.

The inserts are isolated by PCR from the vectors pTG8732 (carrying D64), pTG8733 (R13) and pTG8734

C. Multicopy expression vectors

Figure 2:
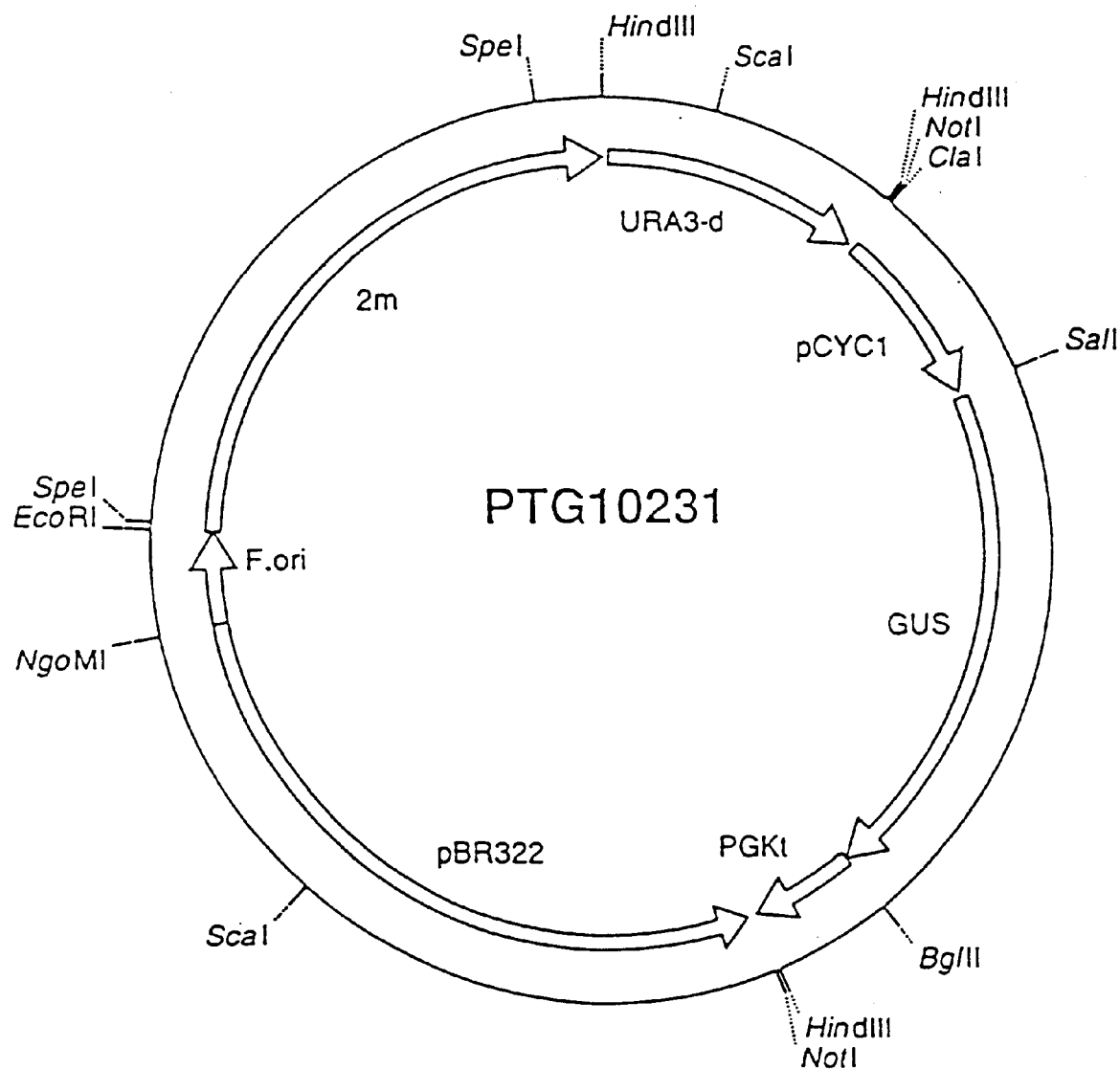
FIG. 2 is a schematic representation of the vector pTG10231 (multicopy vector) comprising the URA3-d gene, the promoter of the CYCl gene (pCYCl), the coding part of the GUS gene, the PGK terminator, a fragment of pBR322 and the phage replication origin F.ori and the yeast replication origin 2μ.

The basic vector designated pTG10231 (FIG. 2; Degryse et al., Yeast, in press) is derived from pTG3828 (Achstetter et al., 1992, supra). It comprises three replication origins, from yeast (2μ), bacteria (ori) and finally phage (f.ori allowing the production of single-stranded DNA) as well as two selectable markers (URA3-d and Amp genes). As a guide, the URA3-d gene corresponds to the URA3 gene deleted of its promoter, thereby ensuring a large number of copies of plasmid in the cell. Finally, it carries an expression cassette in which the sequences encoding the GUS protein (Jefferson et al., 1986, Proc. Natl. Acad. Sci. USA, 83, 8447–8451) are placed under the control of the promoter of the CYC1 gene and of the PGK terminator (Hitzeman et al., 1983, supra). It is within the capability of persons skilled in the art to generate such a vector from the data in the literature.

The vector pTG10231 is digested with ClaI and SalI in order to eliminate the fragment carrying the CYC1 promoter. The amplified fragments (corresponding to the inserts and their respective subfragments) are cloned into the linearized vector. Clones with plasmids having a satisfactory restriction profile, called pTG8784 (carrying D64), pTG8781 (R13), pTG8785 (J1), pTG8782 (R13.2), pTG8783 (R13.3) and pTG8786 (J1.2), are selected.

A negative control is generated by digesting pTG10231 with ClaI and SalI, treating with Klenow and religating. This control, which lacks a promoter, is designated pTG8793.

It is also useful to compare the promoter sequences of the present invention with other promoters, either reputed to be strong, such as those of the MFα1 and PGK genes or weaker such as the promoter of the KEX2 gene (Fuller et al., 1989, Proc. Natl. Acad. Sci. USA, 86, 1434–1438). The corresponding sequences are obtained by PCR:

for the promoter of the KEX2 gene: amplification of a 524 bp fragment from pTG9895 and of the primers oTG6304 (SEQ ID NO: 13) and oTG6293. As a guide, pTG9895 is obtained by inserting into the BamHI site of pTG9852 (Example 1) a PCR fragment carrying the promoter of the KEX2 gene. The latter is amplified from the template pTG4812 (described in EP 396 436) and the oligonucleotides oTG5739 and oTG5740 (SEQ ID NO: 14 and 15), for the promoter of the MFα1 gene: amplification of a 974 bp fragment from a genomic DNA preparation from the FL100 yeast strain (ATCC 28383) and the primers oTG6929 and oTG6930 (SEQ ID NO: 16 and 17), and for the promoter of the PGK gene: amplification of a 779 bp fragment from a genomic DNA preparation from the FL100 yeast strain and the primers oTG7002 and oTG6928 (SEQ ID NO: 18 and 19).

The amplified fragments are then inserted into the ClaI and SalI sites of the vector pTG10231 in place of the CYC1 promoter, to give pTGB780 (KEX2), pTG8789 (MFal) and pTG8791 (PGK), respectively.

D. Single-copy expression vectors

Figure 3:
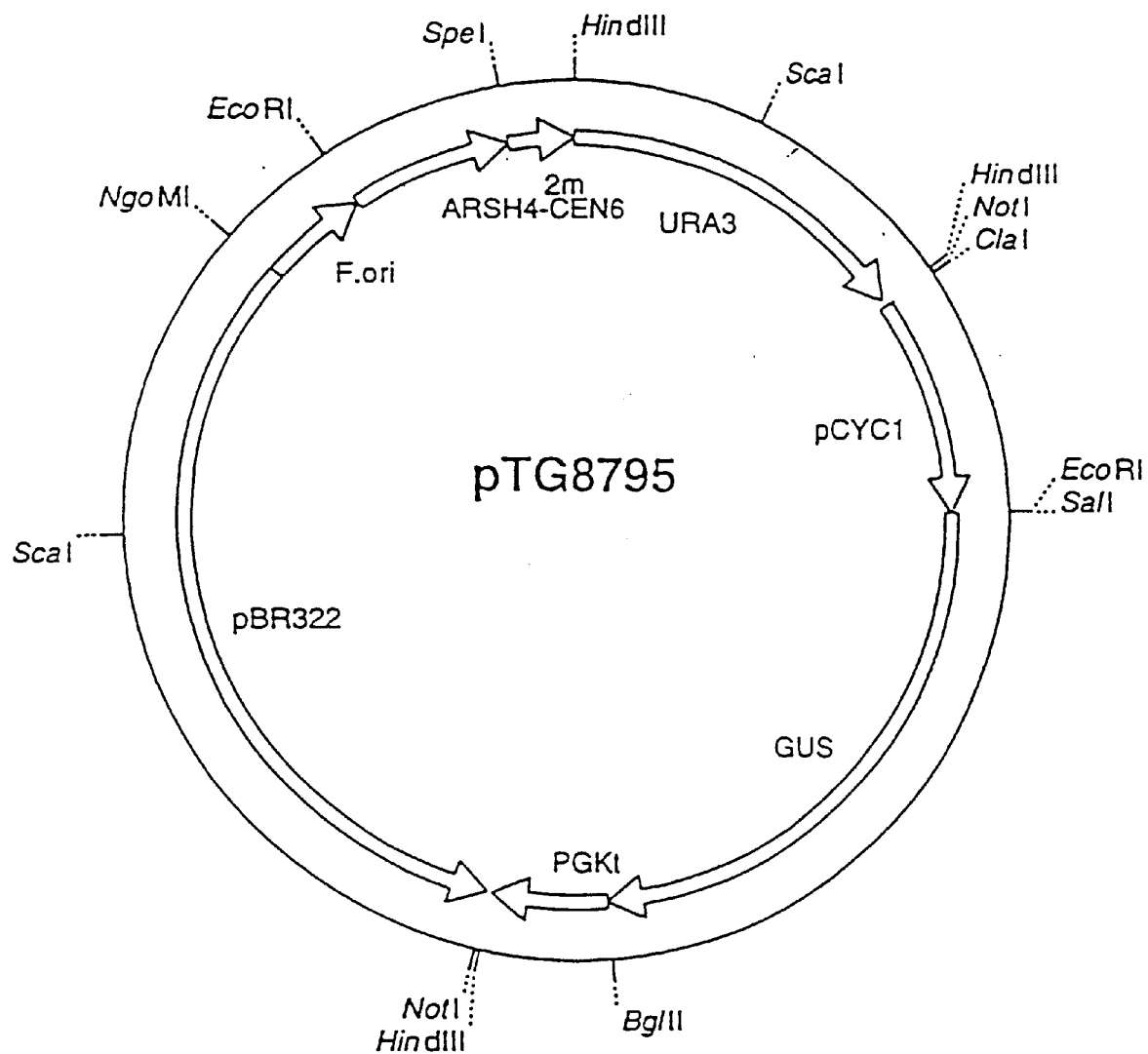
FIG. 3 is a schematic representation of the vector pTG8795 (single copy vector) similar to pTG10231, except that the marker gene consists of the complete URA3 gene and that the ARSH4-CEN6 origin replaces most of the 2μ fragment included in this vector.

The vector pTG8795 (FIG. 3) is equivalent to the vector pTG10231, except that it comprises an autonomous replication unit ARSH6-CEN4 (Sikorski and Hieter, 1989, Genetics, 122, 19–27) in place of the 2 1 origin and the URA3 gene in place of URA3-d.

The promoter fragments are introduced into pTG8795 by homologous recombination by replacing the CYC1 promoter. To do this, the *E. coli* BJ5183 strain (endA, sbcBC, galK, met, thi-1, bioT, hsdr, strR) is co-transformed with one of the plasmids obtained in the preceding stage (donor plasmids pTG8781 to pTG8786) digested with ScaI and, on the other hand, the basic vector pTG8795 (recipient plasmid) linearized with NotI. A first analysis of the restriction profile is made on the clones generated in order to select those exhibiting the expected profile (designated pTG9704 (D64), pTG9701 (R13), pTG9705 (J1), pTG9702 (R13.2), pTG9703 (R13.3) and pTG9706 (J1.2)). Their plasmid content is then transferred into the strain 5K in order to obtain higher quantities of plasmid DNA.

The procedure is carried out similarly in order to generate positive controls using the preceding control vectors (pTG8780 . . . ) as donor vectors. PTG9700 (KEX2), pTG8799 (PGK) and pTG9711 (MFα) are generated. The negative control pTG9713 is obtained from pTG8795 cleaved with the enzymes ClaI and SalI, treated with Klenow and self-ligated.

Example 3

Evaluation of the expression of the GUS gene

The constructs of Example 2C and D are used to transform the strain TGY73.4 or W303α (MATα, ura3, leu2, his3, trp1, ade2; Crivellone et al., 1988, J. Biol. Chem., 263, 14323–14333). The expression of the GUS gene can be evaluated directly on the colonies resulting from the transformation by a semi-quantitative technique described by Hirt (1991, supra) whose protocol was modified as indicated below. A colony portion is collected with a toothpick and deposited on a Nylon N membrane (Amersham). After freezing for 10 min at −80° C., the colonies are thawed on 3M Whatman paper impregnated with 50 mM $Na_2HPO_4$ buffer, pH7, containing 5-bromo-4-chloro-3-indolylglucuronide (X-gluc) reagent at 50 μg/ml (dilution of a stock solution to 5 mg/ml in DMSO, dimethyl sulfoxide). The reaction takes place in the dark at 37° C. The colonies producing the GUS protein appear blue, the intensity and the speed of appearance of the color being higher, the higher the level of expression.

In order to have more quantitative measurements, the transformed yeasts are cultured in liquid medium (YNBG+ cas) at 28° C. A culture sample (10 ml) is collected during growth, the cells are recovered by centrifugation and taken up in 500 μl of GUS extraction buffer supplemented with 1 mM Pefabloc (Jefferson et al., 1987, supra), before being ground for 15 min (Retsch grinder). The ground product is then centrifuged for 10 min at 10,000 rpm at 4° C. The protein concentration is measured on the supernatant (Biorad kit) and the enzymatic activity of the GUS protein determined by fluorimetry using the methylumbelliferyl β-glucuronide substrate. A difference in the protein extraction yields is generally noted between the TGY73.4 and W303α strains. However, the GUS activities, adjusted for the quantity of proteins, are comparable in the two strains.

Figure 4:
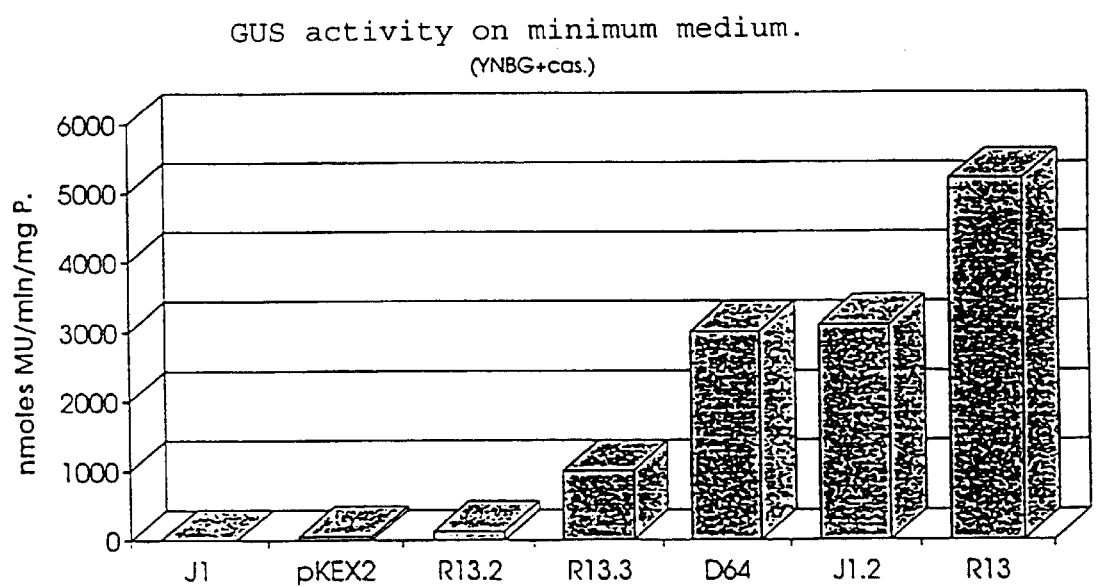
FIG. 4 is a diagram schematically representing the promoter activities of the inserts D64, R13, J1, and their sub-fragments (J1.2, R13.2 and R13.3) in relation to the promoter of the KEX2 gene. The bars represent the level of activity of the GUS protein in the *Saccharomyces cerevisiae* TGY74.3 strain tested in the multicopy system.

FIG. 4 presents the levels of activity of the GUS protein produced in the TGY73.4 strain transformed by the multicopy vectors of Example 2C. As a guide, the samples are collected in the stationary growth phase and the GUS activity is given in nmoles of methylumbelliferon (MU) produced per min and mg of protein. The insert R13 has a promoter activity which is substantially greater than that measured with all the fragments tested as well as the KEX2 promoter (factor 58). The insert D64 can also be considered as a strong promoter in the light of the levels of GUS protein produced under its control (28 times greater than those obtained with the KEX2 promoter). In contrast, the promoter capacities of the complete J1 insert are of the same order of magnitude as KEX2 (to within a factor of 2). However, the deletion of the ORF of 25 aa situated at its 3' end proves advantageous since the promoter activity of the J1.2 subfragment is substantially improved. As for the R13.3 subfragment, it conserves a high promoter activity although less than the complete insert from which it is derived, whereas the R13.2 subfragment constitutes a very weak promoter. Although the data are not represented, no GUS activity is measured with the negative controls (strain TGY73.4 nontransformed or transformed with the plasmid pTG8793).

Figure 5:
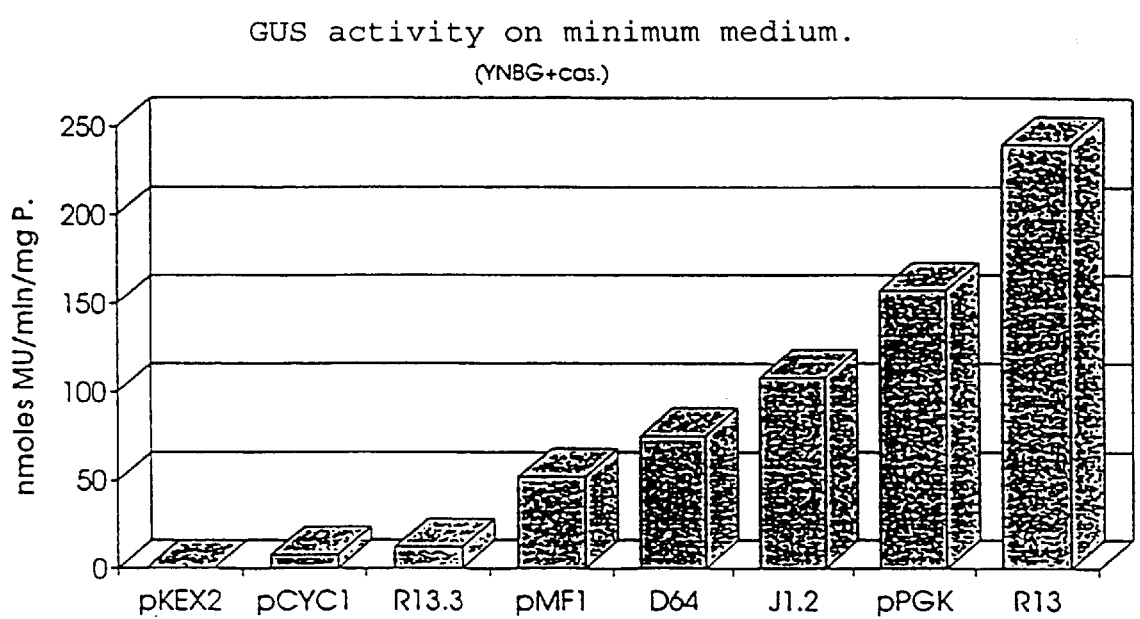
FIG. 5 is a diagram schematically representing the promoter activities of the inserts D64, R13, J1, and their sub-fragments (J1.2, R13.2 and R13.3) in relation to the promoters of the KEX2, PGK, MFα1 (pMF1) and CYCl genes. The bars represent the level of activity of the GUS protein in the *Saccharomyces cerevisiae* TGY74.3 strain tested in the single copy system.

FIG. 5 summarizes the data relating to the single copy vectors of Example 2D (sample collection at an OD 600 nm of about 1). A roughly comparable profile is observed. The GUS activity levels obtained under the control of the complete R13 insert completely exceed those produced from the clones tested as well as the reputedly strong PGK and MFα1 promoters. The promoter activity of the inserts D64 and J1.2 is of the same order of magnitude as that of the reference PGK and MFα1 promoters. Finally, the transcriptional capacity of R13.3, although notable, is less than that determined with the complete insert. In this experiment, the low activity of the CYC1 promoter is explained by the large quantity of glucose in the culture medium because the samples are collected in the exponential phase.

The characterization of the GUS protein produced by the different yeasts transformed was performed using a 7.5% SDS-PAGE gel (mini-protean II dual slab cell system, Biorad). A band with an expected molecular weight (68 kDa) corresponding to the product of expression of the GUS gene, which represents about 5% of the total proteins of the extract, is detected in the yeasts containing pTG8784, pTG8781 and pTG8786, after Comassie blue staining.

The capacity for regulation of these promoter fragments can be studied as a function of the growth and culture conditions (measurement of the activity at various culture times, addition of specific nutrients to the culture medium, such as glucose, thiamin and the like). In particular, the level of GUS activity produced by TGY73.4 strains transformed by the single copy vectors was determined as a function of the growth of the yeasts in minimum medium. The R13 insert is active right at the beginning of the exponential phase and its activity decreases as the OD 600 nm increases. The subfragment J.12 exhibits a similar behaviour. As regards D64, its promoter activity is also lower in the stationary phase but the profile observed is slightly different in the sense that the maximum activity is situated in the middle of the exponential phase (bell-shaped profile). On the other hand, the promoter activity of the R13.3 subfragment is increased in the stationary phase (as is observed with the CYC1 promoter).

In conclusion, these experiments have made it possible to isolate and characterize yeast promoters of variable strength and regulation which are capable of promoting the expression of heterologous genes. cl Example 4

Influence of the culture medium on the promoter activities

Figure 6:
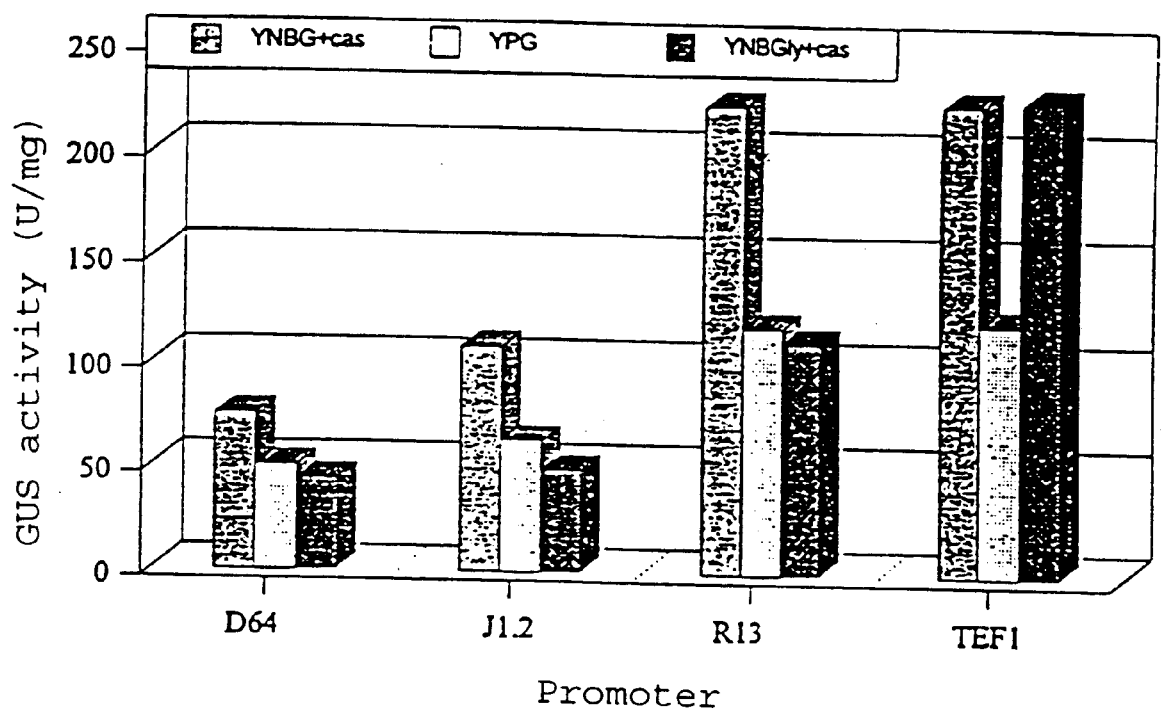
FIG. 6 is a diagram schematically representing the influence of the culture medium on the promoter activities of the inserts D64, J1.2, R13 and, as control, of the TEF1 promoter. The values indicated represent a mean of two samples taken in the growth phase.

The single-copy vectors pTG9704 (D64), pTG9706 (J1.2) and pTG9701 (R13) were cultured in 3 different media, in parallel with the plasmid pTG9707 which is equivalent to those above except that it is the TEF1 promoter (Cottrelle et al., 1985, supra) which directs the expression of the GUS gene. The study is carried out on a glucose-based defined YNBG+cas medium, rich YPG medium and defined oxidative YNBGly+cas medium whose carbon source is glycerol. Two samples are collected in the exponential growth phase ($OD_{600}$~1). The GUS activities are measured by fluorimetry on the acellular protein extracts of each sample (FIG. 6).

The protein extracts of the clones corresponding to the three promoter inserts of the invention all exhibit a GUS activity reduced by 50% on YNBGly+cas medium, in comparison with the glucose-containing YNBG+cas medium. In contrast, the GUS activity controlled by pTEF1 is identical on the YNBG+cas and YNBGly+cas media, confirming that this promoter is efficient on the two carbon sources contained in these culture media. On the other hand, independently of the construct (including pTG9707), the GUS activity is lower on YPG than on YNBG+cas.

The optimum activity of the promoter fragments D64, J1.2 and R13 appears to be obtained on defined medium with glucose as carbon source. However, as indicated above (Example 3), the activity decreases regularly during growth as the glucose disappears from the culture medium (reduction of the level of GUS production by a factor of 2 in the stationary phase). It is indicated that on defined glycerol-containing medium (YNBGly+cas), such a variation in activity is not observed during cell growth (constant GUS level).

Example 5

Study of subfraaments of the insert R13

Progressive deletions in 5' were made on the R13 fragment with the aim of identifying a promoter insert having a minimum size and an optimum activity. The fragment R13.9 is amplified by PCR using pTG9701 (Example 2D) with the aid of oTG 7659 and oTG 7234 (SEQ ID No: 20 and 21) and makes it possible to generate pTG9754 after cloning in the form of a ClaI-SalI fragment in the single-copy expression vector for the GUS gene. R13.9 corresponds to R13 deleted of 80 bp in 5'. The insert R13.5 is also amplified by PCR using the template pTG9701 with the aid of the oligonucleotides oTG7422 (SEQ ID No: 22) and oTG7234, and gives rise to the GUS expression vector pTG9719. R13.5 corresponds to a deletion of 190 bp in 5' of the insert R13. The R13.6 subfragment, which is obtained with the aid of the primers oTG7423 (SEQ ID NO: 23) and oTG7234, results from a deletion of 300 bp in 5' of R13. Its cloning into the GUS single-copy expression plasmid generates pTG9720. Finally, the R13.3 fragment, already described, comprises a 450 bp deletion in 5' of R13.

Figure 7:
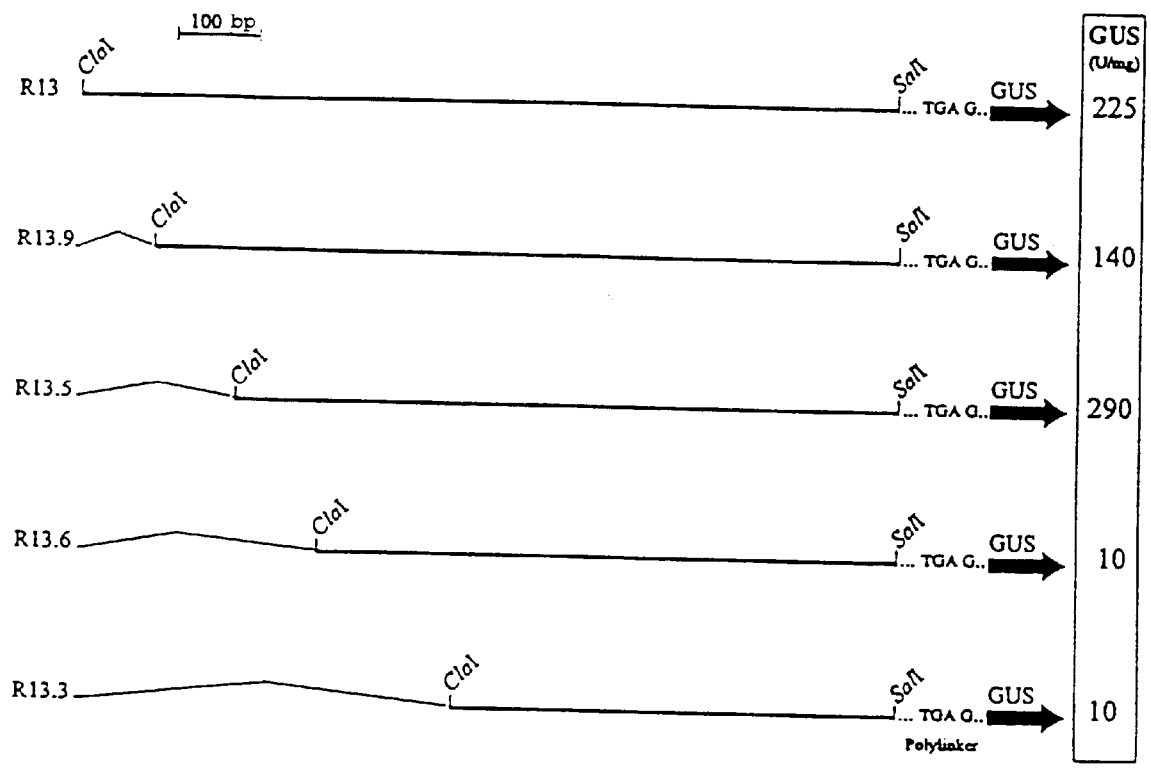
FIG. 7 is a schematic representation of the R13 sub-fragments generated by deletion of the 5' region and of the GUS activity measured for each of them in the single copy expression system and at the beginning of growth.

The TGY73.4 yeasts, respectively transformed by the plasmids pTG9701 (R13), pTG9754 (R13.9), pTG9719 (R13.5), pTG9720 (R13.6) and pTG9703 (R13.3), are cultured on defined YNBG+cas medium and harvested at $OD_{600}$~1. FIG. 7 represents the GUS activities corresponding to the mean values of the fluorimetric measurements at $OD_{600}$~1 (three clones tested per construct).

The original insert R13 has a GUS activity of 225 U/mg in the exponential growth phase. The deletion of about 100 bp in 5' generating R13.9 is accompanied by a loss of activity of about 40% (140 U/mg). On the other hand, the promoter activity increases significantly after an additional deletion of about 100 bp (R13.5) (GUS activity of 290 U/mg exceeding that obtained with R13 and R13.9), which suggests that the deleted region comprises a potential element for negative regulation of gene expression. Finally, additional deletions in 5' (R13.6 and R13.3) considerably reduce the promoter activity (95% loss compared with R13.5). Indeed, the deleted zone contains units of consensus sequences for attachment of the activator/repressor product encoded by the S. cerevisiae RAP1 gene. In conclusion, the R13.5 fragment has a maximum promoter activity which can be used for the expression of the gene of interest.

We claim:

1. An isolated nucleic acid fragment with transcriptional promoter activity, said fragment, comprising all or part of the nucleotide sequence of SEQ ID NO: 1, 2, or 3, or the complement of SEQ ID NO: 1, 2, or 3.

2. A nucleic acid fragment according to claim 1, wherein the nucleotide sequence of said fragment is selected from the group consisting of:

(i) SEQ ID NO: 1, from position 462 to position 1016, (ii) SEQ ID NO: 1, from position 197 to position 1016, and (iii) SEQ ID NO: 3, from position 5 to position 523.

3. Nucleic acid fragment according to claim 1, comprising:

(i) a minimal promoter region; said minimal promoter region being placed downstream of one or more modulatory sequences heterologous to said minimal promoter region, or (ii) at least one modulatory sequence; said modulatory sequence being placed upstream of a minimal promoter region heterologous to said modulatory sequence.

4. An expression cassette comprising a gene of interest placed under the control of a nucleic acid fragment according to claim 1.

5. An expression cassette according to claim 4, wherein the gene of interest encodes a product of expression selected from the group consisting of cytokines, growth factors, receptors, anticoagulants, enzymes or their inhibitors, hormones, antibodies, polypeptides having immunogenic properties, structural proteins, and a selectable marker.

6. An expression vector comprising an expression cassette according to claim 4.

7. An expression vector according to claim 6, wherein said vector is a multicopy or centromeric plasmid vector.

8. A host cell comprising a vector according to claim 6.

9. A host cell comprising an expression cassette according to claim 4.

10. A host cell according to claim 9, wherein said host cell is a lower eukaryotic host cell.

11. A host cell according to claim 10, wherein said host cell is a yeast cell.

12. A host cell according to claim 11, selected from yeasts of the genus Saccharomyces, Schizosaccharomyces, Pichia, Kluyveromyces, Hansenula, Phaffia and Yarrowia.

13. A host cell according to claim 12, wherein said host cell is *Saccharomyces cerevisiae*.

14. A process for the production of a polypeptide of interest comprising (i) culturing a host cell according to claim 9, under appropriate culture conditions allowing the production of said polypeptide of interest and (ii) recovering said polypeptide of interest from the culture of said host cell.

15. A process according to claim 14, wherein the host cell is *Saccharomyces cerevisiae*.

16. A process according to claim 14, wherein the host cell is cultured in a medium comprising glucose as carbon source.

17. An isolated DNA molecule with transcriptional promoter activity, said DNA molecule comprising at least 17 contiguous nucleotides from SEQ ID NO: 1, SEQ ID NO: 2, SEQ ID NO: 3, or sequences complementary to SEQ ID NO: 1, SEQ ID NO: 2, or SEQ ID NO: 3.

18. An isolated DNA molecule with transcriptional promoter activity, said DNA molecule comprising at least 17 contiguous nucleotides from a sequence that hybridizes under stringent conditions with SEQ ID NO: 1, SEQ ID NO: 2, or SEQ ID NO: 3.

* * * * *

SEQUENCE LISTING

<160> NUMBER OF SEQ ID NOS: 23

<210> SEQ ID NO 1
<211> LENGTH: 1016
<212> TYPE: DNA
<213> ORGANISM: Saccharomyces cerevisiae

<400> SEQUENCE: 1

```
gatcaattgt gattccatga actcacaaac aactcgccta agaaactgtc taaattttta      60
tgcactaaat agaccacaaa tgagaacgta aagagaagct tttatcattt tatttctctt     120
ctccttagga ggaaatacaa atatcttttc tacatttaat tcaatctgac agtcaaagtt     180
atacatatac attataccga ttaccaagtt ttcagactag aacccataca ttattttaca     240
```

```
aacccagaca gtacactata caaaaaccca agcaattgca atcaattttt ttgcacgaaa      300
attttattcg aaatcgccaa cccgctagga gaaaagaag gaattctcaa aggagaggct      360
ggacagagag gtcgtcccag tctaccgcct acgagtaatg ttggatacta agcagttccc      420
agcctgaacg ctctgctgga tgggtggaga tttccctcca ggcgggaaca ctcctggtgg      480
attctgctct ggaaactatg cctgtgcatg ctaccaggtt caataatct ttcaatactt      540 gacaaaagta gatatacata ttttaaaga ttagattact attgataaat ctactatttg      600
tcataaactc accaagaaac cacaaagtta ttgaacaatg gtatgtttt tattatatcg      660 cataattatg gcaaatgtta tgaaggattc ctctatgact tagatgtttt gaatcggtac      720
attttatttt cagtatcctt ctgcatatta caaggcaaca tagcagcgga caagaaagcg      780
ttttttgatg ttcgtcttcg aaacgattac tatcagggtc ttttaaatgc tatatcggga      840
cttattgaaa ttgacatatt acacttatga atgacgttgg ctatcaaagt atgagaataa      900
gcctttccta ctattttgta tcatgacaac agggttctgt cgctttgaat gcggcctttt      960
actttgccat attttgataa tgaaaaaact ttcgagaaat atttactaac aggatc       1016

<210> SEQ ID NO 2
<211> LENGTH: 617
<212> TYPE: DNA
<213> ORGANISM: Saccharomyces cerevisiae

<400> SEQUENCE: 2
gatcttgatg tctataccaa ccatgcatga tttcctattg tgcgtgcctt atttacgcac       60 gttttcaac atacggctct atcaccgaag gcgctcaaga gcagaataat atgaccgtca      120
ttcatttcaa acccatacac aatgaacctt atcacaccca acatatgat atggtattaa      180 aaatgaaaa aaattcatta ttctttagcg taattattga agaaaaaaca gtgcgcgcgg      240 taatttttg tcactcagta actagagaga agccgaatgt actcccccgg ctagctggag      300
accatggctc tgcctaggat ttctcttatg ctttcctttc accaatcact tgttccggc       360 gaggctccgc ggagctcgct ttctttcagc ctagcaatca tgttcttgcc agcgtcgtag      420
actactgtat ggcagttgct gcacttgcca tgaatatcct agtgaagcct ctatgcaata      480
atccagttac tgcgttagaa tcctggtaaa atgtctaatc ttattacatt acagcaacgt      540
attagatttt gattgaaaat tagtccttgc gacttggtat atatcttatt ttaagaaagc      600
tgaaaggaag aaagatc                                                    617

<210> SEQ ID NO 3
<211> LENGTH: 609
<212> TYPE: DNA
<213> ORGANISM: Saccharomyces cerevisiae

<400> SEQUENCE: 3
gatcgagaaa aggtcgagat atatttttat ttaaaaattc ttattaatat tagtactatt       60
catgtcataa ctgattacta tttctatctc tgtcagagat ggctagctag aggttgttgc      120
gaagttactt ccaaaagatt ctagactgtg cttacagcat ccatacaccc acccatacat      180
actgatttct tttttttaaag acgtcgattt ttcgaaaaaa gtaaattctc ggcacaggga      240
gttgaattga acttccctgc cccgacggta agcagcttac cggtattgct tcgttctcct      300
tgggagatgt tctcggctct ggaaggaaaa aaccttcgtg gggggagggc tcatatccag      360
taacataggc ggaactcgaa gtgtcagctt acaccgcttc gttctcattg agtgttgagg      420
gattacttgg tatttgaaat acctactaga tttaatgttc gttatagtaa atgatttaat      480
```

```
ttgttcgcta ttacagataa aagaaccata gtcttaagta gtatgttaac gacacaaaag    540
tgtgaaagta gagaagggaa gaacgatgag atccgtcgac ctgcagatca attcgaaatg    600
accgagatc                                                            609
```

<210> SEQ ID NO 4
<211> LENGTH: 30
<212> TYPE: DNA
<213> ORGANISM: Unknown
<220> FEATURE:
<223> OTHER INFORMATION: Description of Unknown Organism:synthetic
      oligonucleotide oTG5427

<400> SEQUENCE: 4

```
ggaagcatat ttgagaagat gcggccagca                                      30
```

<210> SEQ ID NO 5
<211> LENGTH: 31
<212> TYPE: DNA
<213> ORGANISM: Unknown
<220> FEATURE:
<223> OTHER INFORMATION: Description of Unknown Organism:synthetic
      oligonucleotide oTG5428

<400> SEQUENCE: 5

```
attccgaagc ccaacctttc atagaaggcc g                                    31
```

<210> SEQ ID NO 6
<211> LENGTH: 35
<212> TYPE: DNA
<213> ORGANISM: Unknown
<220> FEATURE:
<223> OTHER INFORMATION: Description of Unknown Organism:synthetic
      oligonucleotide oTG6302

<400> SEQUENCE: 6

```
gaagctatcg attttgatgt ctataccaac catgc                                35
```

<210> SEQ ID NO 7
<211> LENGTH: 32
<212> TYPE: DNA
<213> ORGANISM: Unknown
<220> FEATURE:
<223> OTHER INFORMATION: Description of Unknown Organism:synthetic
      oligonucleotide oTG6293

<400> SEQUENCE: 7

```
tggtcggtcg actcgaattg atctgcaggt cg                                   32
```

<210> SEQ ID NO 8
<211> LENGTH: 32
<212> TYPE: DNA
<213> ORGANISM: Unknown
<220> FEATURE:
<223> OTHER INFORMATION: Description of Unknown Organism:synthetic
      oligonucleotide oTG6292

<400> SEQUENCE: 8

```
cttggcatcg atttgtgatt ccatgaactc ac                                   32
```

<210> SEQ ID NO 9
<211> LENGTH: 35
<212> TYPE: DNA
<213> ORGANISM: Unknown
<220> FEATURE:
<223> OTHER INFORMATION: Description of Unknown Organism:synthetic
      oligonucleotide oTG6298

<400> SEQUENCE: 9
gaagctatcg attgagaaaa ggtcgagata tattt                    35

<210> SEQ ID NO 10
<211> LENGTH: 34
<212> TYPE: DNA
<213> ORGANISM: Unknown
<220> FEATURE:
<223> OTHER INFORMATION: Description of Unknown Organism:synthetic
      oligonucleotide oTG6294

<400> SEQUENCE: 10
ttagtagtcg acattactcg taggcggtag actg                     34

<210> SEQ ID NO 11
<211> LENGTH: 36
<212> TYPE: DNA
<213> ORGANISM: Unknown
<220> FEATURE:
<223> OTHER INFORMATION: Description of Unknown Organism:synthetic
      oligonucleotide oTG6301

<400> SEQUENCE: 11
atttccatcg atgcggaaca ctcctggtgg attctg                   36

<210> SEQ ID NO 12
<211> LENGTH: 35
<212> TYPE: DNA
<213> ORGANISM: Unknown
<220> FEATURE:
<223> OTHER INFORMATION: Description of Unknown Organism:synthetic
      oligonucleotide oTG6299

<400> SEQUENCE: 12
tgtgtcgtcg acttactact taagactatg gttct                    35

<210> SEQ ID NO 13
<211> LENGTH: 35
<212> TYPE: DNA
<213> ORGANISM: Unknown
<220> FEATURE:
<223> OTHER INFORMATION: Description of Unknown Organism:synthetic
      oligonucleotide oTG6304

<400> SEQUENCE: 13
gtagctatcg atacgtaata tatttcctca ctttc                    35

<210> SEQ ID NO 14
<211> LENGTH: 35
<212> TYPE: DNA
<213> ORGANISM: Unknown
<220> FEATURE:
<223> OTHER INFORMATION: Description of Unknown Organism:synthetic
      oligonucleotide oTG5739

<400> SEQUENCE: 14
tcttcggatc cttttatttt tactatacat acata                    35

<210> SEQ ID NO 15
<211> LENGTH: 34
<212> TYPE: DNA
<213> ORGANISM: Unknown
<220> FEATURE:
<223> OTHER INFORMATION: Description of Unknown Organism:synthetic
      oligonucleotide oTG5740

<400> SEQUENCE: 15

```
tacttggatc cgtaatatat ttcctcactt tcat                                34

<210> SEQ ID NO 16
<211> LENGTH: 39
<212> TYPE: DNA
<213> ORGANISM: Unknown
<220> FEATURE:
<223> OTHER INFORMATION: Description of Unknown Organism:synthetic
      oligonucleotide oTG6929

<400> SEQUENCE: 16
gaattctatc gataagattt aaaggtattt gacaagtag                           39

<210> SEQ ID NO 17
<211> LENGTH: 37
<212> TYPE: DNA
<213> ORGANISM: Unknown
<220> FEATURE:
<223> OTHER INFORMATION: Description of Unknown Organism:synthetic
      oligonucleotide oTG6930

<400> SEQUENCE: 17
ggaaatgtcg acctttttaat cgtttatatt gtgtatg                            37

<210> SEQ ID NO 18
<211> LENGTH: 40
<212> TYPE: DNA
<213> ORGANISM: Unknown
<220> FEATURE:
<223> OTHER INFORMATION: Description of Unknown Organism:synthetic
      oligonucleotide oTG7002

<400> SEQUENCE: 18
cctgacatcg attcaagacg cacagatatt ataacatctg                          40

<210> SEQ ID NO 19
<211> LENGTH: 38
<212> TYPE: DNA
<213> ORGANISM: Unknown
<220> FEATURE:
<223> OTHER INFORMATION: Description of Unknown Organism:synthetic
      oligonucleotide oTG6928

<400> SEQUENCE: 19
gataaagtcg acgttttat atttgttgta aaaagtag                             38

<210> SEQ ID NO 20
<211> LENGTH: 28
<212> TYPE: DNA
<213> ORGANISM: Unknown
<220> FEATURE:
<223> OTHER INFORMATION: Description of Unknown Organism:synthetic
      oligonucleotide oTG7659

<400> SEQUENCE: 20
gaccacaaat cgatacgtaa agagaagc                                       28

<210> SEQ ID NO 21
<211> LENGTH: 25
<212> TYPE: DNA
<213> ORGANISM: Unknown
<220> FEATURE:
<223> OTHER INFORMATION: Description of Unknown Organism:synthetic
      oligonucleotide OTG7234

<400> SEQUENCE: 21
cacgggttgg ggtttctaca ggacg                                          25
```

```
<210> SEQ ID NO 22
<211> LENGTH: 31
<212> TYPE: DNA
<213> ORGANISM: Unknown
<220> FEATURE:
<223> OTHER INFORMATION: Description of Unknown Organism:synthetic
      oligonucleotide oTG7422

<400> SEQUENCE: 22
cattatatcg attaccaagt tttcagacta g                                  31

<210> SEQ ID NO 23
<211> LENGTH: 36
<212> TYPE: DNA
<213> ORGANISM: Unknown
<220> FEATURE:
<223> OTHER INFORMATION: Description of Unknown Organism:synthetic
      oligonucleotide oTG7423

<400> SEQUENCE: 23
attcgaaatc gataacccgc taggagaaaa agaagg                             36
```